United States Patent [19]

Dumont

[11] 3,976,070
[45] Aug. 24, 1976

[54] NEEDLE REINFORCING MEANS FOR SMALL GAUGE HYPODERMIC NEEDLES

[76] Inventor: Mark Dumont, 3335 Dunbar St., Vancouver, British Columbia, Canada

[22] Filed: Feb. 25, 1975

[21] Appl. No.: 552,758

Related U.S. Application Data

[63] Continuation of Ser. No. 437,396, Jan. 28, 1974, abandoned.

[52] U.S. Cl. .............................................. 128/221
[51] Int. Cl.² ............................................ A61M 5/00
[58] Field of Search ............... 128/215, 218 N, 221, 128/214.4, 2 B

[56] References Cited

UNITED STATES PATENTS

| 268,996 | 12/1882 | Brinkerhoff | 128/221 |
|---|---|---|---|
| 1,125,887 | 1/1915 | Schimmel | 128/221 |
| 1,384,355 | 7/1921 | Smith | 128/221 |
| 1,592,462 | 7/1926 | MacGregor | 128/221 X |
| 1,774,707 | 9/1930 | Gau | 128/221 |
| 2,187,259 | 1/1940 | Barnhart | 128/221 |
| 2,484,657 | 10/1949 | Son | 128/221 X |
| 3,406,687 | 10/1968 | Moyer | 128/221 |
| 3,539,034 | 11/1970 | Tafeen | 128/221 |
| 3,727,613 | 4/1973 | Sorenson et al. | 128/221 X |
| 3,774,606 | 11/1973 | Norton | 128/221 X |
| 3,893,445 | 7/1975 | Hofsess | 128/221 X |

FOREIGN PATENTS OR APPLICATIONS

| 651,436 | 10/1937 | Germany | 128/221 |

Primary Examiner—John D. Yasko
Attorney, Agent, or Firm—Richard E. Babcock, Jr.

[57] ABSTRACT

A support device for a hypodermic needle particularly useful in dental surgery. One part of the support device is a funnel-like structure adapted to fit over the base of the hypodermic needle, and the other part consists of a siding tip guard adapted to slide coaxially inside the funnel-like structure in the manner of an expansible telescope. Both the funnel-like structure and the tip guard have longitudinal openings therethrough, inside which the hypodermic needle is placed. At the end of the tip guard, away from the funnel-like structure, there is an enlarged hub adapted to press against the gum in the mouth of the patient and through which the hypodermic needle is inserted, through the gum and into the bony structure below.

2 Claims, 3 Drawing Figures

NEEDLE REINFORCING MEANS FOR SMALL GAUGE HYPODERMIC NEEDLES

This is a continuation of my prior application, Ser. No. 437,396, filed Jan. 28, 1974, now abandoned.

This invention relates to needle reinforcing means for small gauge hypodermic needles.

For certain types of dental surgery and treatment, it is necessary to make anaesthetic injections into the bony support of the teeth rather than merely into the surrounding gum tissue. It has been customary to make injections of anaesthetic into such bony structure by means of drilling a hole into the bone with a dental drill and injecting the anaesthetic into such hole, in the same general manner as if an injection were being made into soft tissue. The drilling of a hole into a bony structure of a patient is hazardous and has disadvantages. Drill breakage can create great discomfort for the patient and the actual injection may be accompanied by leakage of the anaesthetic around the needle. Moreover, the drilling procedure causes a great deal of local irritation and some bleeding and this may obscure the place where the anaesthetic injection is to be made.

Moreover, it is desirable when making an anaesthetic injection into the bone to use as small amount of anaesthetic as possible. The procedure previously used involved the use of a fairly large amount of anaesthetic.

It is a principal object of the present invention to overcome the troublesome and painful procedure that was customarily used in the past.

An additional object is to provide for instantaneous and painless anaesthesia of regions of the teeth.

A related object of the present invention is to avoid the anaesthesia of tissue in connection with anaesthetizing inside bone structure with consequent elimination of lip biting and cheek biting.

It is also an object of the present invention to protect the point of the hypodermic needle used in the operation by retaining it out of sight and out of contact with the patient until the injection has been made.

It is also an important object of the present invention to accomplish anaesthesia with a minute amount of anaesthetic, and accompanying this object the present invention is of particular advantage for use on patients with known allergies to anaesthetic.

Furthermore, since only a small amount of anaesthetic is used the duration of the anaesthetic is for a minimum period, in most cases anaesthesia is practically gone when the patient leaves the office.

The present invention in its preferred embodiment consists of a 2-part support means for a hypodermic needle. One part of the support means is a funnel-like support member or structure adapted to fit over the base of the hypodermic needle, and the other part consists of a sliding guard sleeve adapted to slide coaxially inside the funnel-like structure in the manner of an expansible telescope. Both the funnel-like structure and the guard sleeve have longitudinal openings therethrough, inside which the hypodermic needle is placed. At the end of the guard sleeve, away from the funnel-like support member, there is an enlarged hub adapted to press against the gum in the mouth of the patient and through which the hypodermic needle is inserted, through the gum and into the bony structure below.

The invention will now be described with reference to the accompanying drawings wherein a preferred embodiment is shown. It will be appreciated that the drawings and accompanying description are by way of example and variations are possible within the scope of the appended claims.

In the drawings wherein the same numbers denote like parts in all figures.

Figure 1:
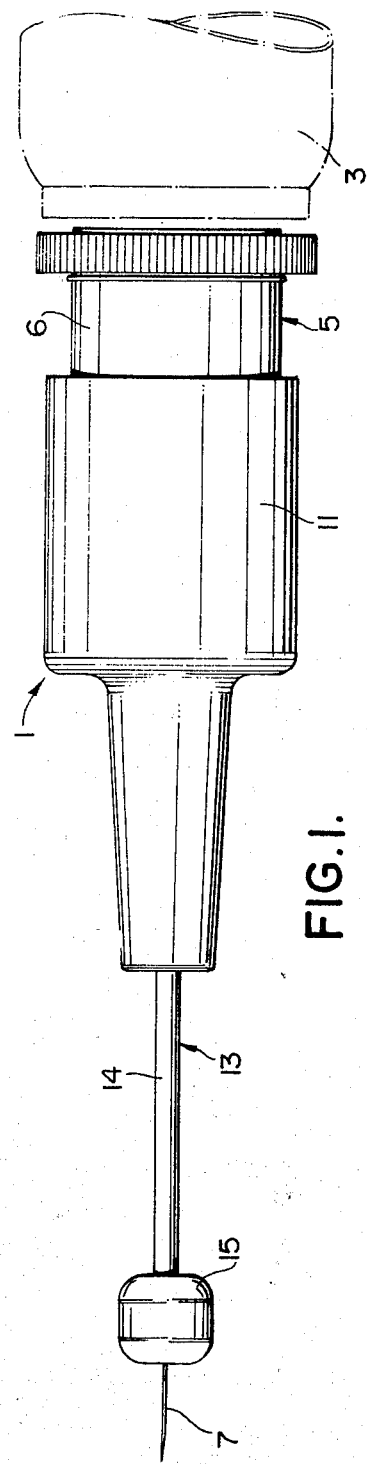
FIG. 1 shows a general view of the needle support device as used with a hypodermic needle, and a hypodermic syringe.

Referring now to the drawings, the needle support device is shown generally at 1. A hypodermic syringe in connection with which the embodiment of the present invention is used is shown at 3 and is indicated by broken lines, as the syringe itself forms no part of the present invention. A conventional hypodermic needle is shown at 5. The base of hypodermic needle 5 is indicated by 6, and the tip of hypodermic needle 5 is shown at 7. The hypodermic needle 5 itself likewise forms no part of the present invention.

The funnel-like structure or support member is shown at 11. Member 11 is adapted to fit snugly over the base 6 of the hypodermic needle 5. A needle guard sleeve is denoted by 13. It is contemplated that guard sleeve 13 will have a telescopic sliding relationship with base support 11. Guard sleeve 13 is made up of a shaft denoted by 14 and an enlarged hub at the outer extremity of shaft 14 denoted by 15. It is contemplated that hypodermic needle 5 will pass through guard sleeve 13.

As has been mentioned, base support 11 and guard sleeve 13 have a telescopic sliding relationship. It is contemplated that guard sleeve 13 will in its initial position be displaced from base support 11 to the extent that it covers the tip 7 of the hypodermic needle 5, not only protecting the tip 7 from damage, but slidably encompassing a major portion of the length of the needle, and thus leaving no appreciable length thereof exposed when the hypodermic needle is in use; this prevents undue flexing of the hypodermic needle when it is inserted into bony structure in the mouth of the patient. FIG. 1 may be regarded as illustrating the position of the apparatus when the hypodermic needle is in use, and the tip 7 protrudes from hub 15.

Figure 2:
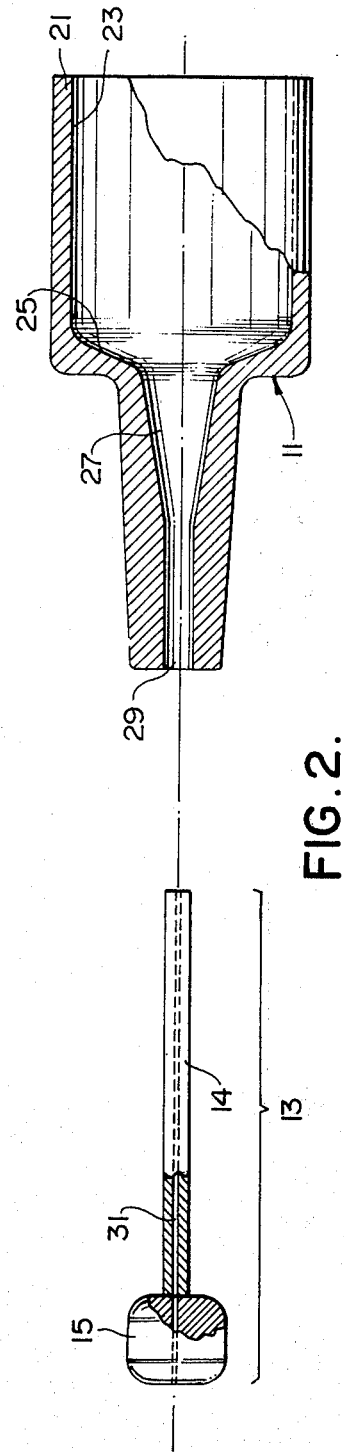
FIG. 2 shows an "exploded", partly cross-sectioned view of the device illustrated in FIG. 1.

Referring now particularly to FIG. 2, the base support 11 has an open-ended portion having a cylindrical wall denoted by 21 of more or less uniform thickness and of inside diameter adapted to fit snugly over the base 6 of the hypodermic needle 5. The interior of wall 21 curves inwardly at 25 and tapers at 27, merging so as to form a cylindrical bore at 29, which is adapted to receive shaft member 14 of tip guard 13. The guard sleeve 13 has outside diameter such that it fits snugly inside cylindrical portion 29 of and base support 11, so as to provide a smooth sliding fit.

As already mentioned, hub 15 is attached at the end of guard sleeve 13 remote from the rear end of that sleeve that coacts with base support 11. Hub 15 is simply an enlarged structure with smooth outside contours so as to protect the delicate surfaces of the mouth of the patient. Through the interior of sleeve 13 is a longitudinal cylindrical opening denoted by 31 of size adapted to receive the hypodermic needle 5 and is sized so that there will be a smooth sliding fit between hypodermic needle 5 and the inside diameter of opening 31. With such smooth sliding fit, the hypodermic needle will be able to resist the tendency to bend or buckle to which it would otherwise be subjected when the tip 7 is being pressed into the bony structure of the patient's mouth.

Figure 3:
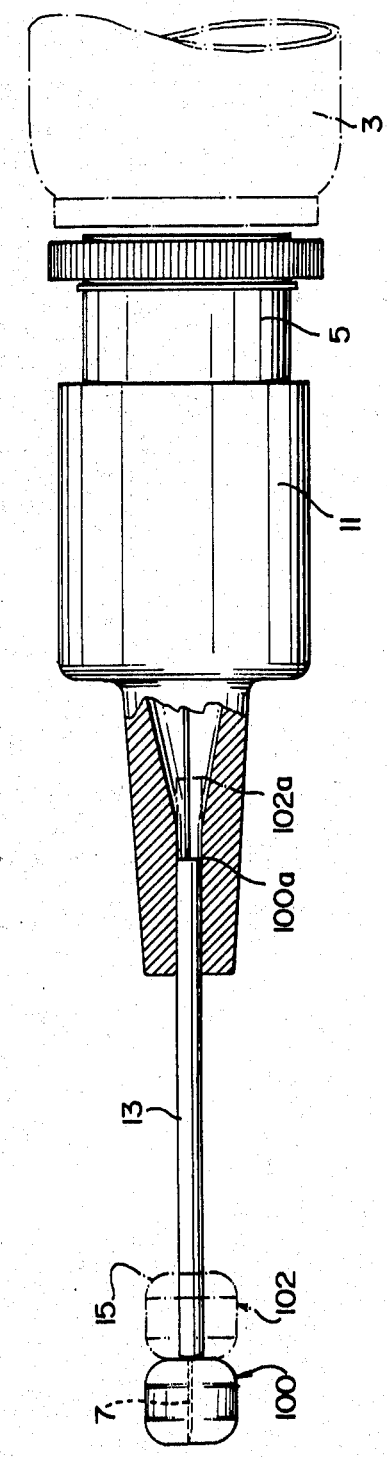
FIG. 3 shows a 2-position view corresponding to FIG. 1, indicating the two main positions occupied by the device when in use.

FIG. 3 indicates the two principal relative positions of the components of base support 1. Reference numeral 100 indicates the position of tip guard 13 before the hypodermic needle 5 is used and in this position the tip 7 fully covered by hub 15. As the hypodermic needle is pressed into the gum of the patient and into the bony structure underneath the gum the forward end of guard sleeve 13 slides or is retracted telescopically into the base support 11 until it occupies the position shown at 102, which is substantially the same as that shown in FIG. 1.

While guard sleeve 13 moves from position 100 to position 102, the rear end of guard sleeve 13 slides from its initial position shown at 100a to a new position denoted by 102a. When sleeve 13 slides from position 100a to 102a, it merely slides along hypodermic needle 5 and continues to surround hypodermic needle 5 so that the latter does not flex unduly.

In the manner indicated needle base support 1 encloses and supports hypodermic needle base 5 at all times when needle support 1 is applied to needle base 6. Initially before the tip 7 of hypodermic needle 5 is inserted in the gum of the patient, the hypodermic needle 5 does not need support against flexing, but needle support 1 then performs a useful function of protecting the tip 7 of hypodermic needle 5 from damage.

As the hypodermic syringe is applied to the gum of the patient by longitudinal pressure in a direction to the left as seen in the figures, the hub 15 presses against the gum of the patient and the tip 7 is ejected from hub 15, through the gum and into the bony structure underneath the gum. The gum will be compressed by the pressure of hub 15, and the tip 7 of the hypodermic needle thus has only a very small unsupported length of perhaps a couple of milimeters.

Thus the device described herein performs its protecting functions with efficiency and simplicity.

I claim:

1. In combination with a hypodermic needle affixed to a base at its rear end and having a forwardly directed free tip end remote from said base; a needle support member firmly secured to said base and having a bore therein through which the needle extends, with said free tip end of the needle projecting forwardly from said member; a unitary needle guard sleeve slidably encompassing and having a smooth sliding fit with said needle throughout the entire length of said sleeve and throughout a major portion of the length of said needle, with one end of said sleeve telescopically slidably received in said bore of the needle support member; said needle guard sleeve having a forwardly directed blunt free end projecting from said needle support member and normally being substantially co-terminus with the tip end of said needle, but being partially retractable into said needle support member to expose said tip end of the needle while encompassing and engaging a medial portion of said needle to support the same against bending.

2. The combination of claim 1, in which said blunt free end of the guard sleeve constitutes an enlarged smooth surface portion adapted to press against soft tissue without penetration thereof.

* * * * *